United States Patent
Lehmbeck et al.

(10) Patent No.: US 8,633,010 B2
(45) Date of Patent: Jan. 21, 2014

(54) FUNGAL PEPC INHIBITOR

(75) Inventors: Jan Lehmbeck, Veksoe (DK); Hiroaki Udagawa, Yokohama (JP)

(73) Assignee: Novozymes A/S, Bagsvaerd (DK)

( * ) Notice: Subject to any disclaimer, the term of this patent is extended or adjusted under 35 U.S.C. 154(b) by 126 days.

(21) Appl. No.: 12/742,545

(22) PCT Filed: Dec. 2, 2008

(86) PCT No.: PCT/EP2008/066605
§ 371 (c)(1),
(2), (4) Date: May 12, 2010

(87) PCT Pub. No.: WO2009/071530
PCT Pub. Date: Jun. 11, 2009

(65) Prior Publication Data
US 2010/0273980 A1      Oct. 28, 2010

Related U.S. Application Data

(60) Provisional application No. 61/012,248, filed on Dec. 7, 2007.

(30) Foreign Application Priority Data

Dec. 6, 2007   (EP) ..................... 07122516

(51) Int. Cl.
*C12N 1/00*       (2006.01)
*C12N 15/00*      (2006.01)

(52) U.S. Cl.
USPC .............. 435/254.3; 435/243; 435/254.1; 435/440; 435/455

(58) Field of Classification Search
None
See application file for complete search history.

(56) References Cited

U.S. PATENT DOCUMENTS

| | | | |
|---|---|---|---|
| 5,840,570 A * | 11/1998 | Berka et al. | 435/254.3 |
| 2005/0055746 A1 * | 3/2005 | Michaud et al. | 800/288 |
| 2006/0024782 A1 * | 2/2006 | Lehmbeck et al. | 435/69.1 |

FOREIGN PATENT DOCUMENTS

| EP | 574 347 | 12/1993 |
|---|---|---|
| WO | WO 90/00192 | 10/1990 |
| WO | WO 97/22705 | 6/1997 |

OTHER PUBLICATIONS

Schu et al., The proteinase YscB inhibitor PBI2 gene of yeast and studies on the function of its protein product; Eur J Biochem, vol. 197, No. 1, pp. 1-8, 1991.*

Frederick et al., "Cloning and characterization of pepC, a gene encoding a serine protease from *Aspergillus niger*", Gene, vol. 125, pp. 57-64 (1993).
Schu et al., "The proteinase yscB inhibitor (PB12) gene of yeast and studies on the function of its protein product", European Journal of Biochemistry, vol. 197, No. 1, pp. 1-7 (1991).
Database UniProt Accession No. A1CQR8 "Putative uncharacterized protein" (2007).
Database UniProt Accession No. A2QPN5 "Similarity: the ORF overlaps with *A. niger* ESTs an_2186 precursor" (2007).
Herman et al., "Genome sequencing and analysis of the versatile cell factory *Aspergillus niger* CBS 513.88", Nature Biotechnology, vol. 25, No. 2, pp. 221-231 (2007).
Database UniProt Accession No. Q5B2V5 "Putative uncharacterized protein" (2005).
Database UniProt Accession No. Q4WJ24 "Putative uncharacterized protein" (2005).
Database EMBL Accession No. AB224527 "*Aspergillus oryzae* cDNA, contig sequence: AoEST1375." (2006).
Monad et al., "Secreted proteases from pathogenic fungi", International Journal of Medical Microbiology, vol. 292, No. 5-6, pp. 405-419 (2002).
Van Den Hombergh et al., "Cloning, characterization and expression of pepF, a gene encoding a serine carboxypeptidase from *Aspergillus niger*", Gene, vol. 151, No. 1, pp. 73-79 (1994).
Monreal et al., "ABA modulates the degradation of phosphoenolpyruvate carboxylase kinase in sorghum leaves", FEBS Letters, vol. 581, No. 18, pp. 3468-3472 (2007).
Database EMBL Accession No. AP007161 "*Apsergillus oryzae* RIB40 genomic DNA, SC012" (2005).
Masayuki et al., "Genome sequencing and analysis of *Aspergillus oryzae*", Nature, vol. 438, No. 7071, pp. 1157-1161 (2005).
Search Report issued in corresponding international application No. PCT/EP2008/066605 dated Mar. 12, 2009.

* cited by examiner

*Primary Examiner* — Celine X Qian
*Assistant Examiner* — Addison D Ault
(74) *Attorney, Agent, or Firm* — Michael W. Krenicky

(57) ABSTRACT

The present invention relates to an isolated polypeptide having PepC inhibitory activity as well as to a method for producing a heterologous polypeptide of interest in an *Aspergillus* host cell comprising: (a) cultivating the *Aspergillus* host cell comprising a first and a second nucleic acid sequences under conditions conducive for the expression of the polypeptides encoded by the said first and second nucleic acid sequences, and wherein the first nucleic acid sequence encodes a heterologous polypeptide of interest and the second nucleic acid encodes the inhibitor polypeptide of the invention, and wherein the inhibitor polypeptide is expressed from a recombinant nucleic acid construct resulting in an increased level of the inhibitor polypeptide compared to an *Aspergillus* host cell not comprising the recombinant nucleic acid construct; and (b) recovering the heterologous polypeptide.

6 Claims, No Drawings

SEQUENCE LISTING

<160> NUMBER OF SEQ ID NOS: 20

<210> SEQ ID NO 1
<211> LENGTH: 210
<212> TYPE: DNA
<213> ORGANISM: Aspergillus oryzae

<400> SEQUENCE: 1

```
atgcctctct acaacgtcac acttaagaaa gactctcccc ctgaagagtt ggagaaagcc     60
aaggagcagg ccagggaaaa aggcggaacc atcaagcatg agtacactct tatcaagggt    120
ttcactgtcg agtaccccga ggaccatgtc agtactcttg agtcgagtga ccatatccac    180
gtcgaacagg atcaagaagt aaagacccag                                     210
```

<210> SEQ ID NO 2
<211> LENGTH: 213
<212> TYPE: DNA
<213> ORGANISM: Aspergillus oryzae

<400> SEQUENCE: 2

```
atgccttcat acattgttac gtgcaaggaa aacgcatcgg ctgaggagat tgaagagaca     60
aaacaacatg tcagagacca aggtggtgaa ataacacacg agtattcgct cataaaaggc    120
tttgctgtga cttttcctga tggcgcggtg atgacactcg agtcgcatcc acatgtagca    180
tcagttgagc cggacggtat catgtcaacg caa                                 213
```

<210> SEQ ID NO 3
<211> LENGTH: 267
<212> TYPE: DNA
<213> ORGANISM: Aspergillus oryzae

<400> SEQUENCE: 3

```
atgaagtctc tccccactct gtttctcgga tgcttgtctt tgtctttggc cagtccgatt     60
gtggtcactt atcctataga caccctcca tctgtcctag aggacgcaat ggaatccatc    120
atcagtgccg gtggacggat cactcatagg tttcagttta tcaatggctt ctcggctgac    180
gctcccgaat cggcggttca gcaaatctca gtccaatctg ccaagtacaa tccaacaatt    240
gagaaggacc tcacagtgtc tatccag                                        267
```

<210> SEQ ID NO 4
<211> LENGTH: 70
<212> TYPE: PRT
<213> ORGANISM: Aspergillus oryzae

<400> SEQUENCE: 4

```
Met Pro Leu Tyr Asn Val Thr Leu Lys Lys Asp Ser Pro Pro Glu Glu
1               5                   10                  15

Leu Glu Lys Ala Lys Glu Gln Ala Arg Glu Lys Gly Gly Thr Ile Lys
            20                  25                  30

His Glu Tyr Thr Leu Ile Lys Gly Phe Thr Val Glu Tyr Pro Glu Asp
        35                  40                  45

His Val Ser Thr Leu Glu Ser Ser Asp His Ile His Val Glu Gln Asp
    50                  55                  60

Gln Glu Val Lys Thr Gln
65                  70
```

<210> SEQ ID NO 5
<211> LENGTH: 71

```
<212> TYPE: PRT
<213> ORGANISM: Aspergillus oryzae

<400> SEQUENCE: 5

Met Pro Ser Tyr Ile Val Thr Cys Lys Glu Asn Ala Ser Ala Glu Glu
1               5                   10                  15

Ile Glu Glu Thr Lys Gln His Val Arg Asp Gln Gly Gly Glu Ile Thr
            20                  25                  30

His Glu Tyr Ser Leu Ile Lys Gly Phe Ala Val Thr Phe Pro Asp Gly
        35                  40                  45

Ala Val Met Thr Leu Glu Ser His Pro His Val Ala Ser Val Glu Pro
    50                  55                  60

Asp Gly Ile Met Ser Thr Gln
65                  70

<210> SEQ ID NO 6
<211> LENGTH: 89
<212> TYPE: PRT
<213> ORGANISM: Aspergillus oryzae

<400> SEQUENCE: 6

Met Lys Ser Leu Pro Thr Leu Phe Leu Gly Cys Leu Ser Leu Ser Leu
1               5                   10                  15

Ala Ser Pro Ile Val Val Thr Tyr Pro Ile Asp Thr Pro Pro Ser Val
            20                  25                  30

Leu Glu Asp Ala Met Glu Ser Ile Ile Ser Ala Gly Gly Arg Ile Thr
        35                  40                  45

His Arg Phe Gln Phe Ile Asn Gly Phe Ser Ala Asp Ala Pro Glu Ser
    50                  55                  60

Ala Val Gln Gln Ile Ser Val Gln Ser Ala Lys Tyr Asn Pro Thr Ile
65                  70                  75                  80

Glu Lys Asp Leu Thr Val Ser Ile Gln
                85

<210> SEQ ID NO 7
<211> LENGTH: 29
<212> TYPE: DNA
<213> ORGANISM: Artificial Sequence
<220> FEATURE:
<223> OTHER INFORMATION: PCR primer

<400> SEQUENCE: 7
gacggatcca ccgaagtctc tccccactc                                29

<210> SEQ ID NO 8
<211> LENGTH: 30
<212> TYPE: DNA
<213> ORGANISM: Artificial Sequence
<220> FEATURE:
<223> OTHER INFORMATION: PCR primer

<400> SEQUENCE: 8
gacctcgagc gtacgaatat catttattac                               30

<210> SEQ ID NO 9
<211> LENGTH: 725
<212> TYPE: DNA
<213> ORGANISM: Aspergillus oryzae

<400> SEQUENCE: 9
gacggatcca ccatgaagtc tctccccact ctgtttctcg gatgcttgtc tttgtctttg    60
```

-continued

```
gccagtccga ttgtggtcac ttatcctata gacacccctc catctgtcct agaggacgca     120
atggaatcca tcatcagtgc cgtatgttgt ggacctcaaa ggattctgta ctgacttgac     180
acgctgattg ttttcattcc tagggtggac ggatcactca taggtttcgt gagtacccat     240
gaatctctcc cgttaaaaga ttgtttatat gcgcatcaag gcctaatacg cttccttctg     300
tccagagttt atcaagtatt acttccttcc cccttatcgc tgattcccag ctgcgacttt     360
ctaacagcgt cttagtggct tctcggctga cgctcccgaa tcggcggttc agcaaatctc     420
agtccaatct gccaagtaca atccaacaat gagaaggac ctcacagtgt ctatccagta     480
gtgatcagag ccacggagta taaaaaagct cttcctgcgc atcccaacgg ccgtgctggt     540
ctcgggacta ttcgctcccg ttgcatccca agagccaata cgagcagggc taacgaataa     600
cgggtttggt tgattatgac ctcaagggaa ttgttgcgtt ggtattctaa attcagtagc     660
cctagtagcg cttcgaaatt gttattgttg tgcgtgtaat aaatgatatt cgtacgctcg     720
aggac                                                                725
```

<210> SEQ ID NO 10
<211> LENGTH: 469
<212> TYPE: PRT
<213> ORGANISM: Homo sapiens

<400> SEQUENCE: 10

```
Met Glu Phe Val Leu Ser Trp Val Phe Leu Val Ala Ile Leu Lys Gly
1               5                   10                  15

Val Gln Cys Glu Gly Gln Leu Val Gln Ser Gly Gly Gly Leu Val His
            20                  25                  30

Pro Gly Gly Ser Leu Arg Leu Ser Cys Ala Gly Ser Gly Phe Thr Phe
        35                  40                  45

Ser Ser Tyr Gly Met His Trp Val Arg Gln Ala Pro Gly Lys Gly Leu
    50                  55                  60

Glu Trp Val Ser Gly Ile Gly Thr Gly Gly Thr Tyr Ser Thr Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Met Ala Val Tyr
            100                 105                 110

Tyr Cys Ala Arg Gly Asp Tyr Gly Ser Gly Ser Phe Phe Asp Cys
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Arg Val Glu Pro Lys
225                 230                 235                 240

Ser Cys Asp Lys Thr His Thr Cys Pro Pro Cys Pro Ala Pro Glu Leu
                245                 250                 255
```

```
Leu Gly Gly Pro Ser Val Phe Leu Phe Pro Pro Lys Pro Lys Asp Thr
                260                 265                 270
Leu Met Ile Ser Arg Thr Pro Glu Val Thr Cys Val Val Val Asp Val
            275                 280                 285
Ser His Glu Asp Pro Glu Val Lys Phe Asn Trp Tyr Val Asp Gly Val
290                 295                 300
Glu Val His Asn Ala Lys Thr Lys Pro Arg Glu Gln Tyr Asn Ser
305                 310                 315                 320
Thr Tyr Arg Val Val Ser Val Leu Thr Val Leu His Gln Asp Trp Leu
                325                 330                 335
Asn Gly Lys Glu Tyr Lys Cys Lys Val Ser Asn Lys Ala Leu Pro Ala
            340                 345                 350
Pro Ile Glu Lys Thr Ile Ser Lys Ala Lys Gly Gln Pro Arg Glu Pro
        355                 360                 365
Gln Val Tyr Thr Leu Pro Pro Ser Arg Glu Glu Met Thr Lys Asn Gln
370                 375                 380
Val Ser Leu Thr Cys Leu Val Lys Gly Phe Tyr Pro Ser Asp Ile Ala
385                 390                 395                 400
Val Glu Trp Glu Ser Asn Gly Gln Pro Glu Asn Asn Tyr Lys Thr Thr
                405                 410                 415
Pro Pro Val Leu Asp Ser Asp Gly Ser Phe Phe Leu Tyr Ser Lys Leu
            420                 425                 430
Thr Val Asp Lys Ser Arg Trp Gln Gln Gly Asn Val Phe Ser Cys Ser
        435                 440                 445
Val Met His Glu Ala Leu His Asn His Tyr Thr Gln Lys Ser Leu Ser
    450                 455                 460
Leu Ser Pro Gly Lys
465

<210> SEQ ID NO 11
<211> LENGTH: 20
<212> TYPE: DNA
<213> ORGANISM: Artificial Sequence
<220> FEATURE:
<223> OTHER INFORMATION: PCR primer

<400> SEQUENCE: 11
gcaagggatg ccatgcttgg                                                  20

<210> SEQ ID NO 12
<211> LENGTH: 31
<212> TYPE: DNA
<213> ORGANISM: Artificial Sequence
<220> FEATURE:
<223> OTHER INFORMATION: PCR primer

<400> SEQUENCE: 12
gggctcaacc ttcttgtcca ccttggtgtt g                                     31

<210> SEQ ID NO 13
<211> LENGTH: 29
<212> TYPE: DNA
<213> ORGANISM: Artificial Sequence
<220> FEATURE:
<223> OTHER INFORMATION: PCR primer

<400> SEQUENCE: 13
gtggacaaga aggttgagcc caaatcttg                                        29

<210> SEQ ID NO 14
```

```
<211> LENGTH: 19
<212> TYPE: DNA
<213> ORGANISM: Artificial Sequence
<220> FEATURE:
<223> OTHER INFORMATION: PCR primer

<400> SEQUENCE: 14
catataacca attgccctc                                                    19

<210> SEQ ID NO 15
<211> LENGTH: 1419
<212> TYPE: DNA
<213> ORGANISM: Homo sapiens

<400> SEQUENCE: 15
gatccaccat ggagtttgtg ctgagctggg ttttccttgt tgctatatta aaaggtgtcc        60
agtgtgaggg tcagctggtg caatctgggg gaggcttggt acatcctggg gggtccctga       120
gactctcctg tgcaggctct ggattcacct tcagtagcta tggtatgcac tgggttcgcc       180
aggctccagg aaaaggtctg gagtgggtat caggtattgg tactggtggt ggcacatact       240
ctacagactc cgtgaagggc cgattcacca tctccagaga caatgccaag aactccttgt       300
atcttcaaat gaacagcctg agagccgagg acatggctgt gtattactgt gcaagaggag       360
attactatgg ttcggggagt ttctttgact gctggggcca gggaaccctg gtcaccgtct       420
cctcagcctc caccaagggc ccatcggtct tccccctggc accctcctcc aagagcacct       480
ctgggggcac agcggccctg gctgcctgg tcaaggacta cttccccgaa ccggtgacgg        540
tgtcgtggaa ctcaggcgcc ctgaccagcg gcgtgcacac cttcccggct gtcctacagt       600
cctcaggact ctactccctc agcagcgtgg tgaccgtgcc ctccagcagc ttgggcaccc       660
agacctacat ctgcaacgtg aatcacaagc ccagcaacac caaggtggac aagaaggttg       720
agcccaaatc ttgtgacaaa actcacacat gcccaccgtg cccagcacct gaactcctgg       780
ggggaccgtc agtcttcctc ttccccccaa aacccaagga caccctcatg atctcccgga       840
cccctgaggt cacatgcgtg gtggtggacg tgagccacga agaccctgag gtcaagttca       900
actggtacgt ggacggcgtg gaggtgcata atgccaagac aaagccgcgg gaggagcagt       960
acaacagcac gtaccgtgtg gtcagcgtcc tcaccgtcct gcaccaggac tggctgaatg      1020
gcaaggagta caagtgcaag gtctccaaca aagcccgccc agcccccatc gagaaaacca      1080
tctccaaagc caaagggcag ccccgagaac acaggtgta caccctgccc ccatcccggg       1140
aggagatgac caagaaccag gtcagcctga cctgcctggt caaaggcttc tatcccagcg      1200
acatcgccgt ggagtgggag agcaatgggc agccggagaa caactacaag accacgcctc      1260
ccgtgctgga ctccgacggc tccttcttcc tctatagcaa gctcaccgtg gacaagagca      1320
ggtggcagca ggggaacgtc ttctcatgct ccgtgatgca tgaggctctg cacaaccact      1380
acacgcagaa gagcctctcc ctgtccccgg gtaaatgac                            1419

<210> SEQ ID NO 16
<211> LENGTH: 29
<212> TYPE: DNA
<213> ORGANISM: Artificial Sequence
<220> FEATURE:
<223> OTHER INFORMATION: PCR primer

<400> SEQUENCE: 16
gacctcgagt cactactgga tagacactg                                         29

<210> SEQ ID NO 17
```

<211> LENGTH: 493
<212> TYPE: DNA
<213> ORGANISM: Aspergillus oryzae

<400> SEQUENCE: 17

```
gacggatcca ccatgaagtc tctccccact ctgtttctcg gatgcttgtc tttgtctttg      60
gccagtccga ttgtggtcac ttatcctata gacacccctc catctgtcct agaggacgca     120
atggaatcca tcatcagtgc cgtatgttgt ggacctcaaa ggattctgta ctgacttgac     180
acgctgattg ttttcattcc tagggtggac ggatcactca taggtttcgt gagtacccat     240
gaatctctcc cgttaaaaga ttgtttatat gcgcatcaag gcctaatacg cttccttctg     300
tccagagttt atcaagtatt acttccttcc ccctatcgc tgattcccag ctgcgacttt      360
ctaacagcgt cttagtggct ctcggctga cgctcccgaa tcggcggttc agcaaatctc      420
agtccaatct gccaagtaca atccaacaat tgagaaggac ctcacagtgt ctatccagta    480
gtgactcgag gac                                                        493
```

<210> SEQ ID NO 18
<211> LENGTH: 26
<212> TYPE: DNA
<213> ORGANISM: Artificial Sequence
<220> FEATURE:
<223> OTHER INFORMATION: PCR primer

<400> SEQUENCE: 18

```
tttctagacc caagccgctg ctggaa                                            26
```

<210> SEQ ID NO 19
<211> LENGTH: 29
<212> TYPE: DNA
<213> ORGANISM: Artificial Sequence
<220> FEATURE:
<223> OTHER INFORMATION: PCR primer

<400> SEQUENCE: 19

```
tttgcatgcc gagcgtaacc gctgcctca                                         29
```

<210> SEQ ID NO 20
<211> LENGTH: 9204
<212> TYPE: DNA
<213> ORGANISM: Artificial Sequence
<220> FEATURE:
<223> OTHER INFORMATION: pHUda667 complete sequence

<400> SEQUENCE: 20

```
aattcaagca attcaagcta gcttatggtg ttttgatcat tttaaatttt tatatggcgg      60
gtggtgggca actcgcttgc gcgggcaact cgcttaccga ttacgttagg gctgatatttt    120
acgtaaaaat cgtcaaggga tgcaagacca aaccgttaaa tttccggagt caacagcatc    180
caagcccaag tccttcacgg agaaaccca gcgtccacat cacgagcgaa ggaccacctc     240
taggcatcgg acgcaccatc caattagaag cagcaaagcg aaacagccca agaaaaaggt    300
cggcccgtcg gccttttctg caacgctgat acgggcagc gatccaacca acaccctcca    360
gagtgactag gggcggaaat ttatcgggat taatttccac tcaaccacaa atcacagtcg    420
tccccggtaa tttaacggct gcagacggca atttaacggc ttctgcgaat cgcttggatt    480
ccccgcccct ggccgtagag cttaaagtat gtcccttgtc gatgcgatgt atgaattagc    540
ttatggtgtt ttgatcattt taaattttta tatggcgggt ggtgggcaac tcgcttgcgc    600
gggcaactcg cttaccgatt acgttagggc tgatatttac gtaaaaatcg tcaagggatg    660
```

```
caagaccaaa ccgttaaatt tccggagtca acagcatcca agcccaagtc cttcacggag    720
aaaccccagc gtccacatca cgagcgaagg accacctcta ggcatcggac gcaccatcca    780
attagaagca gcaaagcgaa acagcccaag aaaaaggtcg gcccgtcggc cttttctgca    840
acgctgatca cgggcagcga tccaaccaac accctccaga gtgactaggg gcggaaattt    900
atcgggatta atttccactc aaccacaaat cacagtcgtc cccggtaatt taacggctgc    960
agacggcaat ttaacggctt ctgcgaatcg cttggattcc ccgcccctgg ccgtagagct   1020
taaagtatgt cccttgtcga tgcgatgtat gaattcatgg tgttttgatc attttaaatt   1080
tttatatggc gggtggtggg caactcgctt gcgcgggcaa ctcgcttacc gattacgtta   1140
gggctgatat ttacgtaaaa atcgtcaagg gatgcaagac caaaccgtta aatttccgga   1200
gtcaacagca tccaagccca agtccttcac ggagaaaccc cagcgtccac atcacgagcg   1260
aaggaccacc tctaggcatc ggacgcacca tccaattaga agcagcaaag cgaaacagcc   1320
caagaaaaag gtcggcccgt cggccttttc tgcaacgctg atcacgggca gcgatccaac   1380
caacaccctc cagagtgact aggggcggaa atttatcggg attaatttcc actcaaccac   1440
aaatcacagt cgtccccggt aatttaacgg ctgcagacgg caatttaacg gcttctgcga   1500
atcgcttgga ttccccgccc ctggccgtag agcttaaagt atgtcccttg tcgatgcgat   1560
gtatcacaac atataaatac tggcaaggga tgccatgctt ggagtttcca actcaattta   1620
cctctatcca cacttctctt ccttcctcaa tcctctatat acacaactgg ggatccacca   1680
tgcggctctc cacatcctcc ctcttcttgt ccgtctcctt gctcggaaag ttggccttgg   1740
gcgcgacgtc ggacgattgg aagggtaagg ccatttacca gttgctcacg gaccgattcg   1800
gtcgcgcaga tgactcgacc tcgaactgtt cgaacctctc gaactactgt ggtggcactt   1860
acgagggcat cactaaacat ctcgactaca tctccggtat gggcttcgat gcaatttgga   1920
tttcgccgat ccctaagaac tcggacggtg gataccacgg ttactgggcc acagacttct   1980
atcagctcaa ctcgaacttc ggcgacgagt cgcagttgaa agcgctcatc caggcggccc   2040
atgagcggga catgtatgtc atgctcgatg tggtggcaaa ccacgccggc ccgacttcga   2100
acggatactc gggttacact ttcggtgatg cctccctcta ccatccgaaa tgtaccatcg   2160
attacaacga tcagacatcg atcgaacagt gttgggtcgc cgatgagttg cccgatatcg   2220
acaccgaaaa ctcggacaac gtcgcaatcc tcaacgacat cgtctccggc tgggtgggta   2280
actactcgtt cgatggtatt cggatcgaca ccgtcaagca catccgcaag gacttctgga   2340
caggttacgc cgaagccgcg ggtgtgttcg cgaccggaga ggtgttcaac ggagaccccg   2400
catacgtggg accctatcag aaatacttgc cttccctcat caactatccc atgtactacg   2460
ccctcaacga cgtcttcgtc tcgaagtcga agggtttctc caggatttcc gagatgttgg   2520
gctcgaaccg taacgccttc gaagatactt ccgtcctcac cacgttcgtg gacaaccacg   2580
acaaccctcg attcttgaac tcccagtccg acaaagccct cttcaagaac gcgctcacat   2640
acgtgttgct cggcgaagga atccccatcg tctactatgg atcggaacag ggcttctcgg   2700
gcggtgcaga ccctgccaac cgagaagtcc tctggactac gaactacgac acgtcgtcgg   2760
atctctacca gttcatcaag accgtcaact cggtgcgtat gaagtcgaac aaggcggtgt   2820
acatggacat ttacgtgggc gataacgcgt atgcattcaa gcatggagac gccttggtgg   2880
tcctcaacaa ctacggctcg ggttcgacca accaggtgtc cttctcggtg tcgggaaagt   2940
tcgactccgg cgcctccctc atggatatcg tgtccaacat cacaactact gtctcctcgg   3000
atggcacagt cactttcaac ttgaaggatg gcctcccggc gattttcacc tccgcaactg   3060
```

```
gcggcaccac tacgacggct accccccactg gatccggcag cgtgacctcg accagcaaga    3120
ccaccgcgac tgctagcaag accagcacca gtacgtcatc aacctcctgt accactccca    3180
ccgccgtggc tgtgactttc gatctgacag ctaccaccac ctacggcgag aacatctacc    3240
tggtcggatc gatctctcag ctgggtgact gggaaaccag cgacggcata gctctgagtg    3300
ctgacaagta cacttccagc gacccgctct ggtatgtcac tgtgactctg ccggctggtg    3360
agtcgtttga gtacaagttt atccgcattg agagcgatga ctccgtggag tgggagagtg    3420
atcccaaccg agaatacacc gttcctcagg cgtgcggaac gtcgaccgcg acggtgactg    3480
acacctggcg gtagttaatt aagtcgagat ctagagggtg actgcacct ggcggtagac     3540 aatcaatcca tttcgctata gttaaaggat ggggatgagg gcaattggtt atatgatcat    3600
gtatgtagtg ggtgtgcata atagtagtga aatggaagcc aagtcatgtg attgtaatcg    3660
accgacggaa ttgaggatat ccggaaatac agacaccgtg aaagccatgg tctttccttc    3720
gtgtagaaga ccagacagac agtccctgat ttaccctgca caaagcacta gaaaattagc    3780
attccatcct tctctgcttg ctctgctgat atcactgtca ttcaatgcat agccatgagc    3840
tcatcttaga tccaagcacg taattccata gccgaggtcc acagtggagc agcaacattc    3900
cccatcattg ctttccccag gggcctccca acgactaaat caagagtata tctctaccgt    3960
ccaatagatc gtcttcgctt caaaatcttt gacaattcca agagggtccc catccatcaa    4020
acccagttca ataatagccg agatgcatgg tggagtcaat taggcagtat tgctggaatg    4080
tcggggccag ttggccgggt ggtcattggc cgcctgtgat gccatctgcc actaaatccg    4140
atcattgatc caccgcccac gaggcgcgtc tttgcttttt gcgcggcgtc caggttcaac    4200
tctctcctct agactggaaa cgcaaccctg aagggattct tcctttgaga gatggaagcg    4260
tgtcatatct cttcggttct acggcaggtt tttttctgct ctttcgtagc atggcatggt    4320
cacttcagcg cttatttaca gttgctggta ttgatttctt gtgcaaattg ctatctgaca    4380
cttattagct atggagtcac cacatttccc agcaacttcc ccacttcctc tgcaatcgcc    4440
aacgtcctct cttcactgag tctccgtccg ataacctgca ctgcaaccgg tgccccatgg    4500
tacgcctccg gatcatactc ttcctgcacg agggcatcaa gctcactaac cgccttgaaa    4560
ctctcattct tcttatcgat gttcttatcc gcaaaggtaa ccggaacaac cacgctcgtg    4620
aaatccagca ggttgatcac agaggcatac ccatagtacc ggaactggtc atgccgtacc    4680
gcagcggtag gcgtaatcgg cgcgatgatg gcgtccagtt ccttcccggc cttttcttca    4740
gcctcccgcc atttctcaag gtactccatc tggtaattcc acttctggag atgcgtgtcc    4800
cagagctcgt tcatgttaac agctttgatg ttcgggttca gtaggtcttt gatatttgga    4860
atcgccggct cgccggatgc actgatatcg cgcattacgt cggcgctgcc gtcagccgcg    4920
tagatatggg agatgagatc gtggccgaaa tcgtgcttgt atggcgtcca cggggtcacg    4980
gtgtgaccgg ctttggcgag tgcggcgacg gtggtttcca cgccgcgcag gataggaggg    5040
tgtggaagga cattgccgtc gaagttgtag tagccgatat tgagcccgcc gttcttgatc    5100
ttggaggcaa taatgtccga ctcggactgg cgccagggca tgggatgac  cttggagtcg    5160 tatttccatg gctcctgacc gaggacggat ttggtgaaga ggcggaggtc taacatactt    5220
catcagtgac tgccggtctc gtatatagta taaaaagcaa gaaaggagga cagtggaggc    5280
ctggtataga gcaggaaaag aaggaagagg cgaaggactc accctcaaca gagtgcgtaa    5340
tcggcccgac aacgctgtgc accgtctcct gaccctccat gctgttcgcc atctttgcat    5400
acggcagccg cccatgactc ggccttagac cgtacaggaa gttgaacgcg gccggcactc    5460
```

```
gaatcgagcc accgatatcc gttcctacac cgatgacgcc accacgaatc ccaacgatcg    5520 cacccctcacc accagaactg ccgccgcacg accagttctt gttgcgtggg ttgacggtgc    5580
gcccgatgat gttgttgact gtctcgcaga ccatcagggt ctgcgggaca gaggtcttga    5640
cgtagaagac ggcaccggct ttgcggagca tggttgtcag aaccgagtcc ccttcgtcgt    5700
acttgtttag ccatgagatg tagcccattg atgtttcgta gccctggtgg catatgttag    5760
ctgacaaaaa gggacatcta acgacttagg ggcaacggtg taccttgact cgaagctggt    5820 cttttgagaga gatggggagg ccatggagtg gaccaacggg tctcttgtgc tttgcgtagt    5880
attcatcgag ttcccttgcc tgcgcgagag cggcgtcagg gaagaactcg tgggcgcagt    5940
ttgtctgcac agaagccagc gtcagcttga tagtcccata aggtggcgtt gttacatctc    6000
cctgagaggt agaggggacc ctactaactg ctgggcgatt gctgcccgtt tacagaatgc    6060
tagcgtaact tccaccgagg tcaactctcc ggccgccagc ttggacacaa gatctgcagc    6120
ggaggcctct gtgatcttca gttcggcctc tgaaaggata cccgatttct ttgggaaatc    6180
aataacgctg tcttccgcag gcagcgtctg gactttccat tcatcaggga tggttttttgc   6240 gaggcgggcg cgcttatcag cggccagttc ttcccaggat tgaggcattc tgtgttagct    6300
tatagtcagg atgttggctc gacgagtgta aactgggagt tggcatgagg gttatgtagg    6360
cttctttagc cccgcatccc cctcattctc ctcattgatc ccgggggagc ggatggtgtt    6420
gataagagac taattatagg gttagctgg tgcctagctg gtgattggct ggcttcgccg     6480
aattttacgg gccaaggaaa gctgcagaac cgcggcactg gtaaacggta attaagctat    6540
cagccccatg ctaacgagtt taaattacgt gtattgctga taaacaccaa cagagcttta    6600
ctgaaagatg ggagtcacgg tgtggcttcc ccactgcgat tattgcacaa gcagcgaggg    6660
cgaacttgac tgtcgtcgct gagcagcctg cagtcaaaca tacatatata tcaaccgcga    6720
agacgtctgg ccttgtagaa cacgacgctc cctagcaaca cctgccgtgt cagcctctac    6780
ggttgttact tgcattcagg atgctctcca gcgggcgagc tattcaaaat attcaaagca    6840
ggtatctcgt attgccagga ttcagctgaa gcaacaggtg ccaaggaaat ctgcgtcggt    6900
tctcatctgg gcttgctcgg tcctggcgta gatctagagt cgacctgcag gcatgcgtaa    6960
tcatggtcat agctgtttcc tgtgtgaaat tgttatccgc tcacaattcc acacaacata    7020
cgagccggaa gcataaagtg taaagcctgg ggtgcctaat gagtgagcta actcacatta    7080
attgcgttgc gctcactgcc cgctttccag tcgggaaacc tgtcgtgcca gctgcattaa    7140
tgaatcggcc aacgcgcggg gagaggcggt ttgcgtattg ggcgctcttc cgcttcctcg    7200
ctcactgact cgctgcgctc ggtcgttcgg ctgcggcgag cggtatcagc tcactcaaag    7260
gcggtaatac ggttatccac agaatcaggg gataacgcag gaaagaacat gtgagcaaaa    7320
ggccagcaaa aggccaggaa ccgtaaaaag gccgcgttgc tggcgttttt ccataggctc    7380 cgccccctg acgagcatca caaaaatcga cgctcaagtc agaggtggcg aaacccgaca     7440
ggactataaa gataccaggc gtttccccct ggaagctccc tcgtgcgctc tcctgttccg    7500
accctgccgc ttaccggata cctgtccgcc tttctccctt cgggaagcgt ggcgctttct    7560
catagctcac gctgtaggta tctcagttcg gtgtaggtcg ttcgctccaa gctgggctgt    7620
gtgcacgaac cccccgttca gcccgaccgc tgcgccttat ccggtaacta tcgtcttgag    7680
tccaacccgg taagacacga cttatcgcca ctggcagcag ccactggtaa caggattagc    7740
agagcgaggt atgtaggcgg tgctacagag ttcttgaagt ggtggcctaa ctacggctac    7800
actagaagga cagtatttgg tatctgcgct ctgctgaagc cagttacctt cggaaaaaga    7860
```

```
gttggtagct cttgatccgg caaacaaacc accgctggta gcggtggttt ttttgtttgc    7920
aagcagcaga ttacgcgcag aaaaaaagga tctcaagaag atcctttgat cttttctacg    7980
gggtctgacg ctcagtggaa cgaaaactca cgttaaggga ttttggtcat gagattatca    8040
aaaaggatct tcacctagat ccttttaaat taaaaatgaa gttttaaatc aatctatttt    8100
caattcaatt catcattttt tttttattct ttttttttgat ttcggtttct ttgaaatttt   8160
tttgattcgg taatctccga acagaaggaa gaacgaagga aggagcacag acttagattg    8220
gtatatatac gcatatgtag tgttgaagaa acatgaaatt gcccagtatt cttaacccaa    8280
ctgcacagaa caaaaacctg caggaaacga agataaatca tgtcgaaagc tacatataag    8340
gaacgtgctg ctactcatcc tagtcctgtt gctgccaagc tatttaatat catgcacgaa    8400
aagcaaacaa acttgtgtgc ttcattggat gttcgtacca ccaaggaatt actggagtta    8460
gttgaagcat taggtcccaa aatttgttta ctaaaaacac atgtggatat cttgactgat    8520
ttttccatgg agggcacagt taagccgcta aaggcattat ccgccaagta caatttttta    8580
ctcttcgaag acagaaaatt tgctgacatt ggtaatacag tcaaattgca gtactctgcg    8640
ggtgtataca gaatagcaga atgggcagac attacgaatg cacacggtgt ggtgggccca    8700
ggtattgtta gcggtttgaa gcaggcggca gaagaagtaa caaaggaacc tagaggcctt    8760
ttgatgttag cagaattgtc atgcaagggc tccctatcta ctggagaata tactaagggt    8820
actgttgaca ttgcgaagag cgacaaagat tttgttatcg gctttattgc tcaaagagac    8880
atgggtggaa gagatgaagg ttacgattgg ttgattatga cacccggtgt gggtttagat    8940
gacaagggag acgcattggg tcaacagtat agaaccgtgg atgatgtggt ctctacagga    9000
tctgacatta ttattgttgg aagaggacta tttgcaaagg gaagggatgc taaggtagag    9060
ggtgaacgtt acagaaaagc aggctgggaa gcatatttga gaagatgcgg ccagcaaaac    9120
taaaaaactg tattataagt aaatgcatgt atactaaact cacaaattag agcttcaatt    9180
taattatatc agttattacc catg                                           9204
```

US 8,633,010 B2

FUNGAL PEPC INHIBITOR

CROSS-REFERENCE TO RELATED APPLICATIONS

This application is a 35 U.S.C. 371 national application of PCT/EP2008/066605 filed Dec. 2, 2008, which claims priority or the benefit under 35 U.S.C. 119 of European application no. EP 07122516.3 filed Dec. 6, 2007 and U.S. provisional application no. 61/012,248 filed Dec. 7, 2007, the contents of which are fully incorporated herein by reference.

SEQUENCE LISTING

This application contains a Sequence Listing in computer readable form. The computer readable form is incorporated herein by reference.

FIELD OF THE INVENTION

The present invention relates to isolated polypeptides having PepC inhibitory activity. The invention also relates to host cells expressing the PepC inhibitor as well as methods of producing and using the polypeptides.

BACKGROUND OF THE INVENTION

The use of recombinant host cells in the expression of heterologous proteins has in recent years greatly simplified the production of large quantities of commercially valuable proteins, which otherwise are obtainable only by purification from their native sources.

One problem frequently encountered is the high level of proteolytic enzymes produced by a given host cell or in the culture medium. Several examples of host organisms deprived of the ability of producing specific proteolytic compounds have previously been reported. For example, International Patent Application WO 90/00192 describes filamentous fungal hosts incapable of secreting an enzymatically active aspartic proteinase, and EP 574 347 describes *Aspergillus niger* hosts defective in serine proteases of the subtilisin-type, pepC or pepD. Cloning and characterization of the pepC gene of *Aspergillus niger* has been described in Frederick et al., Gene, 125 (1993) 57-64.

So far all known prior art relating to pepC mutants and their use in production of heterologous polypeptides in filamentous fungi, particularly in *Aspergillus*, relate preferably to deletion mutants. This requires genetic manipulation of the host cell. It would therefore be desirable to find other means for reducing activity of specific proteases, e.g. in the form of an inhibitor. It is an object of the present invention to provide an alternative solution by providing a DNA molecule encoding an *Aspergillus* serine protease inhibitor, particularly a PepC inhibitor. In the yeast *Saccharomyces cerevisiae* an inhibitor of the proteinase yscB (pepC homologue) has been described (Schu et al., 1991, Eur. J. Biochem, 197:1-7). This inhibitor was found to be cytoplasmic. The PepC protein in *Aspergillus* is known as a protease produced in the vacuole. However, when *Aspergillus* is used as a production host the problems encountered in relation to PepC is normally that PepC can be found in the supernatant. Depending on the product produced this can be a problem for yield/stability.

SUMMARY OF THE INVENTION

The invention provides a DNA molecule encoding a serine protease inhibitor. More specifically a first aspect of the invention provides an isolated polypeptide having PepC inhibitory activity, selected from the group consisting of:

(a) a polypeptide comprising an amino acid sequence having at least 85%, preferably at least 90%, and most preferably at least 95% identity to the mature polypeptide of SEQ ID NO: 6;

(b) a polypeptide encoded by a polynucleotide that hybridizes under preferably at least high stringency conditions with (i) the mature polypeptide coding sequence of SEQ ID NO: 17, (ii) the cDNA sequence contained in SEQ ID NO: 17, or (iii) a full-length complementary strand of (i) or (ii);

(c) a polypeptide encoded by a polynucleotide comprising a nucleotide sequence having preferably at least at least 85%, more preferably at least 90%, and most preferably at least 95% identity to the mature polypeptide coding sequence of SEQ ID NO: 17;

(d) a variant comprising a substitution, deletion, and/or insertion of one or several amino acids of the mature polypeptide of SEQ ID NO: 6.

In a second aspect the present invention relates to a method for producing a heterologous polypeptide of interest in an *Aspergillus* host cell comprising: (a) cultivating the *Aspergillus* host cell comprising a first and a second nucleic acid sequences under conditions conducive for the expression of the polypeptides encoded by the said first and second nucleic acid sequences, and wherein the first nucleic acid sequence encodes a heterologous polypeptide of interest and the second nucleic acid encodes the inhibitor polypeptide of the invention, and wherein the inhibitor polypeptide is expressed from a recombinant nucleic acid construct resulting in an increased level of the inhibitor polypeptide compared to an *Aspergillus* host cell not comprising the recombinant nucleic acid construct; and (b) recovering the heterologous polypeptide.

In a third aspect the present invention relates to a use of the polypeptide of the invention, for the inhibition of a serine protease of the subtilisin-type in vitro or in vivo.

DETAILED DESCRIPTION OF THE INVENTION

The present invention provides an alternative means for removing undesired protease activity which does not involve genetic manipulation of the gene encoding the protease, e.g. by mutating or deleting the protease gene. Instead it has now been discovered that filamentous fungi, and in particular *Aspergillus* possesses an endogenous inhibitor activity capable of inhibiting serine proteases like PepC. The endogenous PepC inhibitor according to the present invention does not share any substantial degree of identity to any known protease inhibitors. Compared to the yeast proteinase yscB inhibitor, PB12, (Schu, P. Wolf, D. H.; Eur. J. Biochem. 197:1-7 (1991)) the *Aspergillus* PepC inhibitor displays only 19% identity. Furthermore, the inhibitor is secreted and can therefore be found in the supernatant in the growth medium of the host cell. This would not have been expected if compared to the yscB inhibitor which is almost exclusively localised to the cytoplasm (Schu et al., supra).

PepC inhibitory activity: The term "inhibitory activity" is defined herein as a polypeptide that acts as an inhibitor of PepC. An inhibitor is a substance which reversibly or irreversibly prevents the normal action of an enzyme without destroying the enzyme; competitive inhibitors acting by binding to the active site and preventing binding of substrate, and non-competitive inhibitors acting by binding to other parts of the enzyme. PepC inhibitory activity is determined by a radial diffusion assay as described in Materials and Methods according to the procedure described in the examples.

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the PepC inhibitory activity of the mature polypeptide of SEQ ID NO: 6.

Isolated polypeptide: The term "isolated polypeptide" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

Substantially pure polypeptide: The term "substantially pure polypeptide" denotes herein a polypeptide preparation which contains at most 10%, preferably at most 8%, more preferably at most 6%, more preferably at most 5%, more preferably at most 4%, at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation.

The polypeptides of the present invention are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

Mature polypeptide: The term "mature polypeptide" is defined herein as a polypeptide having PepC inhibitory activity that is in its final form following translation and any post-translational modifications, such as N-terminal processing, C-terminal truncation, glycosylation, phosphorylation, etc. In a preferred aspect, the mature polypeptide is amino acids 18 to 89 of SEQ ID NO: 6 based on the SignalP prediction program that predicts amino acids 1 to 17 of SEQ ID NO: 6 to be a signal peptide. This is in accordance with the purified inhibitor displaying an N-terminal of SPIVVTYPID.

Mature polypeptide coding sequence: The term "mature polypeptide coding sequence" is defined herein as a nucleotide sequence that encodes a mature polypeptide having PepC inhibitory activity. In a preferred aspect, the mature polypeptide coding sequence is nucleotides 64 to 141, 204 to 228, 306 to 315, and 416 to 481 of SEQ ID NO: 17 based on the length of the signal sequence and an alignment of the EST sequence, SEQ ID NO: 3 and the genomic DNA sequence SEQ ID NO: 17. Accordingly nucleotides 13 to 63 of SEQ ID NO: 17 encode the predicted signal peptide.

Identity: The relatedness between two amino acid sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Homologous sequence: The term "homologous sequence" is defined herein as a predicted protein that gives an E value (or expectancy score) of less than 0.001 in a tfasty search (Pearson, W. R., 1999, in *Bioinformatics Methods and Protocols*, S. Misener and S. A. Krawetz, ed., pp. 185-219) with the *A. oryzae* PepC inhibitor comprised in SEQ ID NO: 6.

Polypeptide fragment: The term "polypeptide fragment" is defined herein as a polypeptide having one or more (several) amino acids deleted from the amino and/or carboxyl terminus of the mature polypeptide of SEQ ID NO: 6; or a homologous sequence thereof; wherein the fragment has PepC inhibitory activity.

Subsequence: The term "subsequence" is defined herein as a nucleotide sequence having one or more (several) nucleotides deleted from the 5' and/or 3' end of the mature polypeptide coding sequence of SEQ ID NO: 17; or a homologous sequence thereof; wherein the subsequence encodes a polypeptide fragment having PepC inhibitory activity.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic or recombinant nucleotide sequence.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polynucleotide encoding a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the invention, and which is operably linked to additional nucleotides that provide for its expression.

Host cell: The term "host cell", as used herein, includes any cell type which is susceptible to transformation, transfection, transduction, and the like with a nucleic acid construct comprising a polynucleotide of the present invention.

Modification: The term "modification" means herein any chemical modification of the polypeptide consisting of the mature polypeptide of SEQ ID NO: 6; or a homologous sequence thereof; as well as genetic manipulation of the DNA encoding such a polypeptide. The modification can be a substitution, a deletion and/or an insertion of one or more (several) amino acids as well as replacements of one or more (several) amino acid side chains.

Artificial variant: When used herein, the term "artificial variant" means a polypeptide having PepC inhibitory activity produced by an organism expressing a modified polynucleotide sequence of the mature polypeptide coding sequence of SEQ ID NO: 17; or a homologous sequence thereof. The modified nucleotide sequence is obtained through human intervention by modification of the polynucleotide sequence disclosed in SEQ ID NO: 17; or a homologous sequence thereof.

Polypeptides Having PepC Inhibitory Activity

In a first aspect, the present invention relates to isolated polypeptides comprising an amino acid sequence having a degree of identity to the mature polypeptide of SEQ ID NO: 6 of preferably at least 70%, more preferably at least 75%, more preferably at least 80%, more preferably at least 85%, even more preferably at least 90%, most preferably at least 95%, and even most preferably at least 96%, at least 97%, at least 98%, or at least 99%, which have PepC inhibitory activity (hereinafter "homologous polypeptides"). In a preferred aspect, the homologous polypeptides have an amino acid sequence that differs by ten amino acids, preferably by five amino acids, more preferably by four amino acids, even more preferably by three amino acids, most preferably by two amino acids, and even most preferably by one amino acid from the mature polypeptide of SEQ ID NO: 6.

A polypeptide of the present invention preferably comprises the amino acid sequence of SEQ ID NO: 6 or an allelic variant thereof; or a fragment thereof having PepC inhibitory activity. In a preferred aspect, the polypeptide comprises the amino acid sequence of SEQ ID NO: 6. In another preferred aspect, the polypeptide comprises the mature polypeptide of SEQ ID NO: 6. In another preferred aspect, the polypeptide comprises amino acids 18 to 89 of SEQ ID NO: 6, or an allelic variant thereof; or a fragment thereof having PepC inhibitory activity. In another preferred aspect, the polypeptide comprises amino acids 18 to 89 of SEQ ID NO: 6 (corresponding to the predicted mature polypeptide and confirmed by N-terminal sequencing of purified inhibitor). In another preferred aspect, the polypeptide consists of the amino acid sequence of SEQ ID NO: 6 or an allelic variant thereof; or a fragment thereof having PepC inhibitory activity. In another preferred aspect, the polypeptide consists of the amino acid sequence of SEQ ID NO: 6. In another preferred aspect, the polypeptide consists of the mature polypeptide of SEQ ID NO: 6. In another preferred aspect, the polypeptide consists of amino acids 18 to 89 of SEQ ID NO: 6 or an allelic variant thereof; or a fragment thereof having PepC inhibitory activity. In another preferred aspect, the polypeptide consists of amino acids 18 to 89 of SEQ ID NO: 6.

The present invention relates to isolated polypeptides having PepC inhibitory activity which are encoded by polynucleotides which hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 17, (ii) the cDNA sequence contained in the sequence of SEQ ID NO: 17, (iii) a subsequence of (i) or (ii), or (iv) a complementary strand of (i), (ii), or (iii) (J. Sambrook, E. F. Fritsch, and T. Maniatis, 1989, *Molecular Cloning, A Laboratory Manual*, 2d edition, Cold Spring Harbor, N.Y.). A subsequence of SEQ ID NO: 17 contains at least 100 contiguous nucleotides or preferably at least 200 contiguous nucleotides. Moreover, the subsequence may encode a polypeptide fragment which has PepC inhibitory activity.

In one particular embodiment the mature polypeptide coding sequence of SEQ ID NO: 17 comprises nucleotides 64 to 141, 204 to 228, 306 to 315, and 416 to 481 of SEQ ID NO: 17. In another particular embodiment the cDNA sequence contained in SEQ ID NO: 17 comprises nucleotides 13 to 141, 204 to 228, 306 to 315, and 416 to 481 of SEQ ID NO: 17.

The nucleotide sequence of SEQ ID NO: 17 or a subsequence thereof, as well as the amino acid sequence of SEQ ID NO: 6 or a fragment thereof, may be used to design a nucleic acid probe to identify and clone DNA encoding polypeptides having PepC inhibitory activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length.

For example, the nucleic acid probe may be at least 200 nucleotides, preferably at least 300 nucleotides, or more preferably at least 400 nucleotides in length. Both DNA and RNA probes can be used. The probes are typically labeled for detecting the corresponding gene (for example, with 32P, 3H, 35S, biotin, or avidin). Such probes are encompassed by the present invention.

A genomic DNA or cDNA library prepared from such other strains may, therefore, be screened for DNA that hybridizes with the probes described above and encodes a polypeptide having PepC inhibitory activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 17; or a subsequence thereof; the carrier material is preferably used in a Southern blot.

For purposes of the present invention, hybridization indicates that the nucleotide sequence hybridizes to a labeled nucleic acid probe corresponding to the mature polypeptide coding sequence of SEQ ID NO: 17; the cDNA sequence contained in SEQ ID NO: 17; its full-length complementary strand; or a subsequence thereof; under very low to very high stringency conditions. Molecules to which the nucleic acid probe hybridizes under these conditions can be detected using, for example, X-ray film.

In a preferred aspect, the nucleic acid probe is the mature polypeptide coding sequence of SEQ ID NO: 17. In another preferred aspect, the nucleic acid probe is nucleotides 13 to 141, 204 to 228, 306 to 315, and 416 to 481 of SEQ ID NO: 17 (cDNA). In another preferred aspect, the nucleic acid probe is a polynucleotide sequence that encodes the polypeptide of SEQ ID NO: 6, or a subsequence thereof.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In another aspect, the present invention relates to isolated polypeptides having PepC inhibitory activity encoded by polynucleotides comprising or consisting of nucleotide sequences that have a degree of identity to the mature polypeptide coding sequence of SEQ ID NO: 17 of preferably at least 65%, more preferably at least 70%, more preferably at least 75%, more preferably at least 80%, more preferably at least 85%, even more preferably at least 90%, most preferably at least 95%, and even most preferably 96%, 97%, 98%, or 99%, which encode an active polypeptide.

In a further aspect, the present invention relates to artificial variants comprising a conservative substitution, deletion, and/or insertion of one or more (several) amino acids of the mature polypeptide of SEQ ID NO: 6; or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., PepC inhibitory activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309:59-64. The identities of essential amino acids can also be inferred from analysis of identities with polypeptides which are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30:10832-10837; U.S. Pat. No. 5,223,409; WO 92/06204), and region-directed mutagenesis (Derbyshire et al., 1986, *Gene* 46:145; Ner et al., 1988, *DNA* 7:127).

Mutagenesis/shuffling methods can be combined with high-throughput, automated screening methods to detect activity of cloned, mutagenized polypeptides expressed by host cells. Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of the mature polypeptide of SEQ ID NO: 6, such as amino acids 18 to 89 of SEQ ID NO: 6, is 10, preferably 9, more preferably 8, more preferably 7, more preferably at most 6, more preferably 5, more preferably 4, even more preferably 3, most preferably 2, and even most preferably 1.

Sources of Polypeptides Having PepC Inhibitory Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted.

A polypeptide of the present invention may be a fungal polypeptide, and more preferably a filamentous fungal polypeptide such as an *Acremonium*, *Aspergillus*, *Aureobasidium*, *Cryptococcus*, *Filobasidium*, *Fusarium*, *Humicola*, *Magnaporthe*, *Mucor*, *Myceliophthora*, *Neocallimastix*, *Neurospora*, *Paecilomyces*, *Penicillium*, *Piromyces*, *Schizophyllum*, *Talaromyces*, *Thermoascus*, *Thielavia*, *Tolypocladium*, or *Trichoderma* polypeptide.

In another preferred aspect, the polypeptide is an *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, *Aspergillus oryzae*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola insolens*, *Humicola lanuginosa*, *Mucor miehei*, *Myceliophthora thermophila*, *Neurospora crassa*, *Penicillium purpurogenum*, *Trichoderma harzianum*, *Trichoderma koningii*, *Trichoderma longibrachiatum*, *Trichoderma reesei*, or *Trichoderma viride* polypeptide.

In another preferred aspect, the polypeptide is an *Aspergillus oryzae*, or *Aspergillus niger* polypeptide.

In a more preferred aspect, the polypeptide is an *Aspergillus oryzae* polypeptide, and most preferably a *Aspergillus oryzae* (NBRL4177) polypeptide, e.g., the polypeptide of SEQ ID NO: 6 or the mature polypeptide comprised in SEQ ID NO: 6. It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), Agricultural Research Service Patent Culture Collection, Northern Regional Research Center (NRRL) and National Institute of Technology and Evaluation Biological Resource Center (NBRC).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of another microorganism. Once a polynucleotide sequence encoding a polypeptide has been detected with the probe(s), the polynucleotide can be isolated or cloned by utilizing techniques which are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Polynucleotides

The polypeptides having PepC inhibitory activity of the present invention are encoded by isolated polynucleotides described below.

In a preferred aspect, the nucleotide sequence comprises or consists of SEQ ID NO: 17. In another preferred aspect, the nucleotide sequence comprises or consists of the mature polypeptide coding sequence of SEQ ID NO: 17. In another preferred aspect, the nucleotide sequence comprises or consists of the cDNA sequence contained in SEQ ID NO: 17, particularly the cDNA consists of nucleotides 13 to 141, 204 to 228, 306 to 315, and 416 to 481 of SEQ ID NO: 17. The present invention also encompasses nucleotide sequences that encode polypeptides comprising or consisting of the amino acid sequence of SEQ ID NO: 6 or the mature polypeptide thereof, which differ from SEQ ID NO: 17 or the mature polypeptide coding sequence thereof by virtue of the degeneracy of the genetic code. The present invention also relates to subsequences of SEQ ID NO: 17 that encode fragments of SEQ ID NO: 6 that have PepC inhibitory activity.

The present invention also relates to mutant polynucleotides comprising or consisting of at least one mutation in the mature polypeptide coding sequence of SEQ ID NO: 17, in which the mutant nucleotide sequence encodes the mature polypeptide of SEQ ID NO: 6.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Aspergillus*, or another or related organism and thus, for example, may be an allelic or species variant of the polypeptide encoding region of the nucleotide sequence.

The present invention also relates to isolated polynucleotides comprising or consisting of nucleotide sequences that have a degree of identity to the mature polypeptide coding sequence of SEQ ID NO: 17 of at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identity, which encode an active polypeptide.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the mature polypeptide coding sequence of SEQ ID NO: 17, e.g., a subsequence thereof, and/or by introduction of nucleotide substitutions that do not give rise to another amino acid sequence of the polypeptide encoded by the nucleotide sequence, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, supra). In the latter technique, mutations are introduced at every positively charged residue in the molecule, and the resultant mutant molecules are tested for PepC inhibitory activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, supra; Smith et al., 1992, supra; Wlodaver et al., 1992, supra).

The present invention also relates to isolated polynucleotides encoding polypeptides of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 17, (ii) the cDNA sequence contained in SEQ ID NO: 17, or (iii) a full-length complementary strand of (i) or (ii); or allelic variants and subsequences thereof. (Sambrook et al., 1989, supra), as defined herein. In a preferred aspect, the complementary strand is the full-length complementary strand of the mature polypeptide coding sequence of SEQ ID NO: 17.

The present invention also relates to isolated polynucleotides obtained by (a) hybridizing a population of DNA under very low, low, medium, medium-high, high, or very high stringency conditions with (i) the mature polypeptide coding sequence of SEQ ID NO: 17, (ii) the cDNA sequence contained in SEQ ID NO: 17, or (iii) a full-length complementary strand of (i) or (ii); and (b) isolating the hybridizing polynucleotide, which encodes a polypeptide having PepC inhibitory activity. In a preferred aspect, the complementary strand is the full-length complementary strand of the mature polypeptide coding sequence of SEQ ID NO: 17.

Nucleic Acid Constructs

The present invention also relates to nucleic acid constructs comprising an isolated polynucleotide of the present invention operably linked to one or more control sequences which direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence which is recognized by a host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1,ADH2/GAP), *Saccharomyces cerevisiae* triose phosphate isomerase (TPI), *Saccharomyces cerevisiae* metallothionine (CUP1), and *Saccharomyces cerevisiae* 3-phosphoglycerate kinase. Other useful promoters for yeast host cells are described by Romanos et al., 1992, Yeast 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for Aspergillus oryzae TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C(CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, Saccharomyces cerevisiae alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in trans-lation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

In a preferred aspect, the signal peptide coding region is nucleotides 13 to 63 of SEQ ID NO: 17, which encode amino acids 1 to 17 of SEQ ID NO: 6.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described above may be joined together to produce a recombinant expression vector which may include one or more convenient restriction sites to allow for insertion or substitution of the nucleotide sequence encoding the polypeptide at such sites. Alternatively, a nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

A conditionally essential gene may function as a non-antibiotic selectable marker. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98:61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention, which are advantageously used in the recombinant production of the PepC inhibitor and optionally another polypeptide of interest. Particularly this other polypeptide of interest is a heterologous polypeptide susceptive to PepC degradation. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980). In an even more preferred aspect, the yeast host cell is a Candida, Hansenula, Kluyveromyces, Pichia, Saccharomyces, Schizosaccharomyces, or Yarrowia cell. In a most preferred aspect, the yeast host cell is a Saccharomyces carlsbergensis, Saccharomyces cerevisiae, Saccharomyces diastaticus, Saccharomyces douglasii, Saccharomyces kluyveri, Saccharomyces norbensis or Saccharomyces oviformis cell. In another most preferred aspect, the yeast host cell is a Kluyveromyces lactis cell. In another most preferred aspect, the yeast host cell is a Yarrowia lipolytica cell. In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as Saccharomyces cerevisiae is by budding of a unicellular thallus and carbon catabolism may be fermentative. In an even more preferred aspect, the filamentous fungal host cell is an Acremonium, Aspergillus, Aureobasidium, Bjerkandera, Ceriporiopsis, Coprinus, Coriolus, Cryptococcus, Filobasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes, or Trichoderma cell. In a most preferred aspect, the filamentous fungal host cell is an Aspergillus awamori, Aspergillus fumigatus, Aspergillus foetidus, Aspergillus japonicus, Aspergillus nidulans, Aspergillus niger or Aspergillus oryzae cell. In another most preferred aspect, the filamentous fungal host cell is a Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, or Fusarium venenatum cell. In another most preferred aspect, the filamentous fungal host cell is a Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, or Ceriporiopsis subvermispora, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei, or Trichoderma viride cell.

Fungal cells may be transformed by a process involving protoplast formation, transformation of the protoplasts, and regeneration of the cell wall in a manner known per se. Suitable procedures for transformation of Aspergillus and Trichoderma host cells are described in EP 238 023 and Yelton et al., 1984, Proceedings of the National Academy of Sciences USA 81: 1470-1474. Suitable methods for transforming Fusarium species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, Journal of Bacteriology 153: 163; and Hinnen et al., 1978, Proceedings of the National Academy of Sciences USA 75: 1920.

Methods of Production

The present invention also relates to methods for producing a polypeptide of the present invention, comprising (a) cultivating a cell, which in its wild-type form is capable of producing the polypeptide, under conditions conducive for production of the polypeptide; and (b) recovering the polypeptide. Preferably, the cell is of the genus Aspergillus, and more preferably Aspergillus oryzae.

The polypeptide of the invention could in another embodiment be produced recombinantly from a nucleic acid construct as described previously. In a further embodiment the present invention therefore relates to methods for producing a polypeptide of the present invention, comprising (a) cultivating a host cell comprising a nucleic acid construct of the invention under conditions conducive for production of the polypeptide; and (b) recovering the polypeptide.

Particularly the PepC inhibitor can be expressed in a host cell co-expressing a heterologous polypeptide of interest. More particularly the heterologous polypeptide of interest is susceptible to degradation by PepC, thereby increasing the yield of the heterologous polypeptide compared to a host cell which does not express the PepC inhibitor. This method of producing a heterologous polypeptide is an alternative to using a mutant of pepC gene, e.g. a deletion mutant. For this particular purpose the PepC inhibitor polypeptide of the invention should preferably be expressed at a higher level than normal. The PepC inhibitor is normally present in the host cell and despite this PepC is still a problem when expressing certain heterologous polypeptides. In a preferred embodiment the PepC inhibitor should therefore be overexpressed, preferably from a strong promoter. In order to be able to control the level of expression the PepC inhibitor could either be expressed from an inducible promoter or from a constitutive promoter. In one particular embodiment the endogenous copy of the gene encoding the PepC inhibitor could be inactivated. Preferably the PepC inhibitor is therefore expressed from a recombinant nucleic acid construct. In this embodiment the promoter controlling PepC inhibitor expression is a foreign promoter. By "foreign" is meant a promoter not normally controlling the expression of pepC.

In a further embodiment the present invention therefore relates to a method for producing a heterologous polypeptide of interest in an *Aspergillus* host cell comprising: (a) cultivating the *Aspergillus* host cell comprising a first and a second nucleic acid sequences under conditions conducive for the expression of the polypeptides encoded by the said first and second nucleic acid sequences, and wherein the first nucleic acid sequence encodes a heterologous polypeptide of interest and the second nucleic acid encodes the inhibitor polypeptide of the invention, and wherein the inhibitor polypeptide is expressed from a recombinant nucleic acid construct resulting in an increased level of the inhibitor polypeptide compared to an Aspergillus host cell not comprising the recombinant nucleic acid construct; and (b) recovering the heterologous polypeptide.

Particularly suitable promoters to be used for controlling the expression of the PepC inhibitor can be selected from the group consisting of promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

The exact level of PepC inhibitor needed in order to inactivate PepC in the supernatant may vary. The skilled person will know how to select suitable promoters and as described herein PepC activity can be measured. When a heterologous polypeptide of interest is degraded by PepC the skilled person can test available promoters in order to find a level of expression that will provide the necessary inhibition. This may vary depending on the polypeptide of interest and growth conditions.

In a particular embodiment the heterologous polypeptide is an antibody. Particularly the antibody is IgG, more particularly IgG1.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors.

EXAMPLES

Materials and Methods
Materials
Strains
*E. coli* DB6507 (ATCC 35673)
*Aspergillus oryzae* NBRC4177 (IF04177): available from Institute for fermentation, Osaka; 17-25 Juso Hammachi 2-Chome Yodogawa-Ku, Osaka, Japan.
JaL507 is described in WO20060211089, example 2.
JaL601 is described in example 3.
JaL909 is described in example 5.
JaL940 is described in example 7.
JaL942 is described in example 7.
PM-8 is described in WO2001051646 example 7
JaL1182 is described in example 12.
JaL1157 and JaL1158 are described in example 13.
Genes
pyrG: This gene codes for orotidine-5'-phosphate decarboxylase, an enzyme involved in the biosynthesis of uridine.
niaD: This gene codes for nitrate reductase, an enzyme involved in the metabolism of nitrate.

The V039 protein is described in WO2006069290, example 4, table 5. It is a fusion protein composed of the *Rhizomucur pusillus* α-amylase catalytic domain, an *Aspergillus niger* amyloglycosidase linker sequence, and a carbon binding modul (CBM).

Furthermore, an *Aspergillus niger* alpha-amylase signal described in patent WO8901969, claim 17 is used as the signal sequence. The complete sequence of the expression construct, pHUda667, and an explanation of the individual elements contained therein is described in example 11.

Plasmids
pJaL485 is described in patent WO2003008575, example 3.
pJaL1030 is described in example 6.
pJaL1035 is described in example 2.
pJaL790 is described in WO2005070962, example 1.
pNZ-3 is described in WO2005070962, example 2.
pNZ-4 is described in WO2005070962, example 3.
pJaL1000 is described in example 8.
pHUda737 is described in example 9.
pHUda753 is described in example 10.
pHUda667 is described in example 11.
Primer and DNA Sequences
EST ZY029357 (SEQ ID NO: 1)
EST ZY097797 (SEQ ID NO: 2)
EST ZY106022 (SEQ ID NO: 3)
AA ZY029357 (SEQ ID NO: 4)
AA ZY097797 (SEQ ID NO: 5)
AA ZY106022 (SEQ ID NO: 6)
Primer ZY106022-b (SEQ ID NO: 7)
Primer ZY106022-c (SEQ ID NO: 8)
ZY106022 DNA (SEQ ID NO: 9)
IgG1 amino acids (SEQ ID NO: 10)
Primer 8653 (SEQ ID NO: 11)
Primer FG-30 (SEQ ID NO: 12)
Primer FG-31 (SEQ ID NO: 13)
Primer 8654 (SEQ ID NO: 14)
IgG1 DNA (SEQ ID NO:15)
Primer ZY106022-d (SEQ ID NO: 16)
ZY106022 genome DNA (SEQ ID NO: 17)
Primer opyrGF (SEQ ID NO: 18)
Primer opyrGR (SEQ ID NO: 19)
pHUda667 (SEQ ID NO: 20)

Methods

General methods of PCR, cloning, ligation nucleotides etc. are well-known to a person skilled in the art and may for example be found in "Molecular cloning: A laboratory manual", Sambrook et al. (1989), Cold Spring Harbor lab., Cold Spring Harbor, N.Y.; Ausubel, F. M. et al. (eds.); "Current protocols in Molecular Biology", John Wiley and Sons, (1995); Harwood, C. R., and Cutting, S. M. (eds.); "DNA Cloning: A Practical Approach, Volumes I and II", D. N. Glover ed. (1985); "Oligonucleotide Synthesis", M. J. Gait ed. (1984); "Nucleic Acid Hybridization", B. D. Hames & S. J. Higgins eds (1985); "A Practical Guide To Molecular Cloning", B. Perbal, (1984).

Dna Hybridization

In short all DNA hybridisation was carried out for 16 hours at 65° C. in a standard hybridisation buffer of 10×Denhart's solution, 5×SSC, 0.02 M EDTA, 1% SDS, 0.15 mg/ml polyA RNA and 0.05 mg/ml yeast tRNA. After hybridisation the filters were washed in 2×SSC, 0.1% SDS at 65° C. twice and exposed to X-ray films.

PCR Amplification

All PCR amplifications were performed in a volume of 100 microL containing 2.5 units Taq polymerase, 100 ng of pSO2, 250 nM of each dNTP, and 10 pmol of each of the two primers described above in a reaction buffer of 50 mM KCl, 10 mM Tris-HCl pH 8.0, 1.5 mM MgCl2. Amplification was carried out in a Perkin-Elmer Cetus DNA Termal 480, and consisted of one cycle of 3 minutes at 94° C., followed by 25 cycles of 1 minute at 94° C., 30 seconds at 55° C., and 1 minute at 72° C.

*Aspergillus* Transformation

*Aspergillus* transformation was done as described by Christensen et al.; Biotechnology 1988, 6:1419-1422. In short, *A. oryzae* mycelia were grown in a rich nutrient broth. The mycelia were separated from the broth by filtration. 50 mg of β-glucanase enzyme (GLUCANEX™ Novozymes A/S, Bagsvaerd, Denmark) was added to the mycelia in osmotically stabilizing buffer such as 1.2 M MgSO$_4$ buffered to pH 5.0 with sodium phosphate. The suspension was incubated for 60 minutes at 37 degrees C. with agitation. The protoplasts were filtered through mira-cloth to remove mycelial debris. The protoplasts were harvested and washed twice with STC (1.2 M sorbitol, 10 mM CaCl$_2$, 10 mM Tris-HCl pH 7.5). The protoplasts were finally resuspended in 200-1000 microl STC.

For transformation, 5 microg DNA was added to 100 microl protoplast suspension and then 200 microl PEG solution (60% PEG 4000, 10 mM CaCl$_2$, 10 mM Tris-HCl pH 7.5) was added and the mixture was incubated for 20 minutes at room temperature. The protoplast were harvested and washed twice with 1.2 M sorbitol. The protoplast was finally re-suspended 200 microl 1.2 M sorbitol. Transformants containing an intact niaD gene were selected for its ability to used nitrate as the sole source for nitrogen on minimal plates (Cove D. J. 1966. Biochem. Biophys. Acta. 113:51-56) containing 1.0 M sucrose as carbon source, 10 mM Sodium nitrate as nitrogen source. After 4-5 days of growth at 37 degrees C., stable transformants appeared as vigorously growing and sporulating colonies. Transformants were purified twice through conidiospores.

LB Skim Milk Agar Plates

Is LB-medium containing 1% skim milk (Difco 232100) and 1.5% Bacto-agar.

Protease inhibitor assay was done by radial diffusion

The sample (20 μl) to be analysed was loaded into a punched hole in the LB skim milk agar plate. The plate(s) was incubated 20 hours at 37 C. Subsequently the halo was measured.

PepC Protease Containing Fermentation Broth

The pepC protease containing fermentation broth was prepared as described in WO2005070962, example 15, fermentation method J3.

ELISA for Determination of Intact Human IgG

Intact IgG was determined using an ELISA which uses goat anti-human IgG (Fc specific) as the capture antibody and goat anti-human kappa chain conjugated with alkaline phosphatase as the detection antibody. As standard was used a human myeloma IgG1, kappa purified from human plasma. The ELISA procedure was a standard protocol.

Antibody Stability Test

Fermentation broth was incubated for 24 hours at room temperature and the intact antibody was determined by ELISA.

Media and Reagents

Cove-N: 342.3 g/L Sucrose, 20 ml/L COVE salt solution, 3 g/L NaNO$_3$, 30 g/L noble agar. Cove salt solution: per liter 26 g KCl, 26 g MgSO$_4$-7H$_2$O, 76 g KH$_2$PO$_4$, 50 ml Cove trace metals. Cove trace metals: per liter 0.04 g NaB$_4$O$_7$-10H$_2$O, 0.4 g CuSO$_4$-5H$_2$O, 1.2 g FeSO$_4$-7H$_2$O, 0.7 g MnSO$_4$—H$_2$O, 0.7 g Na$_2$MoO$_2$-2H$_2$O, 0.7 g ZnSO$_4$-7H$_2$O.

YPG: 4 g/L Yeast extract, 1 g/L $KH_2PO_4$, 0.5 g/L $MgSO_4$-$7H_2O$, 5 g/L Glucose, pH 6.0.

STC: 0.8 M Sorbitol, 25 mM Tris pH 8, 25 mM $CaCl_2$.

STPC: 40% PEG4000 in STC buffer.

Cove-N top agarose: 342.3 g/L Sucrose, 20 ml/L COVE salt solution, 3 g/L $NaNO_3$, 10 g/L low melt agarose.

MLC (glucose 40 g/L, soy bean powder 50 g/L, citric acid 4 g/L, pH 5.0)

MU-1(Malt dextrin 260 g/L, $MgSO_4.7H_2O$ 3 g/L, $K_2SO_4$ 6 g/L, $KH_2PO_4$ 5 g/L, Trace metal solution 0.5 m/L, Urea 2% (w/v), pH 4.5)

Example 1

Identification of *Asperqillus oryzae* pepC Inhibitors

A tBLASTn search with the *Saccharomyces cerevisiae* proteinase yscB inhibitor (PBI2) amino acids (aa) sequence (UNIPROT:PO1095) against an *Aspergillus oryzae* EST database three different ESTs were identified as putative homologues of the yeast yscB inhibitor. The three ESTs ZY029357 (SEQ ID NO: 1), ZY097797 (SEQ ID NO: 2) and ZY106022 (SEQ ID NO: 3) are encoding proteins with the length of 70 aa (SEQ ID NO: 4), 71 aa (SEQ ID NO: 5) and 89 aa (SEQ ID NO: 6), respectively. The homology is shown in table 1.

TABLE 1

|  | 1 | 2 | 3 | 4 |
|---|---|---|---|---|
| ZY029357: 1 | 100 | | | |
| ZY097797: 2 | 43 (55) | 100 | | |
| ZY106022: 3 | 26 (34) | 21 (35) | 100 | |
| yscB: 4 | 34 (47) | 30 (42) | 19 (32) | 100 |

% identical position (x): % consensus position

Comparing the 3 *A. oryzae* EST's showed that the ZY106022 has a putative signal sequence according to signalP (Bendtsen J D, Nielsen H, von Heijne G and Brunak S (2004) Improved prediction of signal peptides—SignalP 3.0. J. Mol. Biol., 340:783-795) on 23 amino acids (position 1-23 in SEQ ID NO: 4). This indicates that the protein (inhibitor) is secreted. For the other two putative inhibitors no signal sequence was found, which indicated that they are located intracellularly.

Example 2

Construction of *Aspergillus* Expression Cassette for ZY106022 pJaL1035

The *Aspergillus* expression cassette pJaL1035, suitable for expression of a gene of interest under the control of the *A. niger* neutral amylase promoter (NA2), and the *A. niger* glucoamylse terminator and having a truncated 3' part of the *A. oryzae* niaD gene which allows a single cross-over event with an *Aspergillus* niaD mutant having only the 5' part of the niaD gene thereby resulting in an intact niaD for selection of growth on nitrate (a system comparable with that described in Gomi K, limura Y and Hara S (1987) Integrative transformation of *Aspergillus oryzae* with a plasmid containing the *Aspergillus nidulans* argB gene. Agric. Boil. Chem. 51:2549-2555) was constructed in the following way:

A 719 by fragment was amplified by PCR with *A. oryzae* genomic DNA as template and the primers ZY106022-b (SEQ ID NO: 7) and ZY106022-c (SEQ ID NO: 8). This was digested with BamHI and XhoI resulting in a 715 by fragment (SEQ ID NO: 9). The 715 BamHI-XhoI fragment was cloned into the BamHI-SalI sites of pJaL485, resulting in plasmid pJaL1035.

Example 3

Construction of the pyrG Minus *A. oryzae* Strain, JaL601

For removing the defect pyrG gene located in the alkaline protease gene in the *A. oryzae* strain JaL507 the following was done:

The *A. oryzae* strain JaL507 was screened for resistance to 5-fluoro-orotic acid (FOA) to identify spontaneous pyrG mutants on minimal plates (Cove D. J. 1966. Biochem. Biophys. Acta. 113:51-56) supplemented with 1.0 M sucrose as carbon source, 10 mM sodium nitrate as nitrogen source, and 0.5 mg/ml FOA. One strain, JaL601, was identified as being pyrGminus. JaL601 is uridine dependent, therefore it can be transformed with the wild type pyrG gene and transformants selected by the ability to grow in the absence of uridine.

Example 4

Expression of ZY106022 in *Asperqillus oryzae*

The strain JaL601 was transformed with expression plasmid pJaL1035 as described in the methods section.

Shake flask containing 10 ml YPM medium (2 g/l yeast extract, 2 g/l peptone, and 2% maltose) was inoculated with spores from 10 transformants and the mother strain JaL601 and incubated at 30 degrees C., 200 rpm for 4 days.

Example 5

Detection of Expression of the Inhibitor ZY106022 by Inhibiting the PepC Protease Detection of expression of the putative PepC protease inhibitor was done by showing that no or a reduced halo was produce by the pepC protease on 1% skim milk agar plates.

The protease inhibitor assay was done by mixing 10 µl PepC fermentation broth with 10 µl supernatant from a transformant expressing the PepC inhibitor from pJaL1035 (see example 4) and as a control 10 µl PepC fermentation broth with 10 µl fermentation broth (YPM medium). Incubation was performed at room temperature for 30 min. The 20 µl was loaded into a punched hole in the LB skim milk agar plate. The plate(s) was incubated 20 hours at 37 C. Subsequently the halo was measured. These results show that some transformants produced no halo or a halo that is smaller than the control halo. This shows that ZY106022 is an *A. oryzae* PepC inhibitor. One transformant (JaL909) that produces sufficient inhibitor, ZY106022, so that no halo could be seen was chosen for further experiments.

Example 6

Construction of a Native IgG1 Heavy-Chain *Aspergillus* Expression Plasmid pJaL1030

A human IgG1 heavy chain amino acids sequence SEQ ID NO: 10 was modified so that the arginine at position 236 was change to lysine by SOE PCR. A first sequence was amplified by PCR using plasmid pNZ-3 as template and the forward primer 8653 (SEQ ID NO: 11) and the reverse primer FG-30 (SEQ ID NO: 12) resulting in a product of 805 bp. A second sequence was amplified by PCR using plasmid pNZ-3 as template and the forward primer FG-31 (SEQ ID NO: 13) and the reverse primer 8654 (SEQ ID NO: 14) resulting in a product of 795 bp. The two PCR fragment was mixed and a third PCR was made with forward primer 8653 and reverse primer 8654 resulting in a product of 1600 bp. The PCR product of 1600 by was purified and cut with the restriction endonucleases BamHI and XhoI. The resulting 1419 by fragment (SEQ ID NO: 15) was cloned into the corresponding site in pJaL790 to create pJaL1030. The sequence of the insert in pJaL1030 was verified by sequencing.

Example 7

Expression of IgG1 Antibody in *Aspergillus oryzae* Strain JaL909

The *Aspergillus oryzae* strains JaL909 was transformed with a one to one ratio of the expression plasmid pJaL1030, and NZ-4 described by Christensen et al.; Biotechnology 1988 6 1419-1422.

A shake flask containing 10 ml YPM medium (2 g/l yeast extract, 2 g/l peptone, and 2% maltose) was inoculated with spores from the generated transformants and the host JaL909 and incubated at 30 C, with shaking (200 rpm) for 4 days.

The supernatants were screened by ELISA for intact IgG1 as described in the methods section. Two transformants named JaL940 and JaL942 were selected for lab-tank fermentation. Fermentation was done as described in WO2005070962, example 15, method J3. Samples from the last part of the fermentation were checked for protease activity on skim milk agar plates as described in the methods section. Results showed that JaL940 displayed a halo the same size as the control, whereas for JaL942 no halo was seen similar to the mother strain, JaL909. This indicates that JaL940 has lost the gene copies of the inhibitor ZY106022. Southern blot was used to confirm this. The blot showed that JaL909 has more than one copy integrated at the niaD locus and JaL942 has retained this gene number, whereas JaL940 only has one copy left.

The stability of intact antibody from the strains JaL942, JaL940 and a control strain expressing the antibody in JaL601 is 100%, 50% ad 50%, respectively.

Example 8

Construction of *Aspergillus* Expression Cassette for ZY106022 pJaL1000

The *Aspergillus* expression cassette pJaL1000, suitable for expressing a gene of interest under the control of the *A. niger* neutral amylase promoter (NA2), the *A. niger* glucoamylse terminator and having the *A. nidulans* amdS gene for selection of transformants in *Aspergillus*. A 487 by fragment was amplified by PCR using *A. oryzae* genomic DNA as template and the primers ZY106022-b (SEQ ID NO: 7) and ZY106022-d (SEQ ID NO: 16). The PCR product was digested with BamHI and XhoI resulting in a 481 by fragment (SEQ ID NO: 17). The 481 by BamHI-XhoI fragment was cloned into the BamHI-XhoI sites pJaL790, resulting in plasmid pJaL1000.

Example 9

Construction of pHUda737 Expression Vector

Plasmid pHUda737 comprises an expression cassette based on the *Aspergillus niger* neutral amylase II promoter fused to the *Aspergillus nidulans* triose phosphate isomerase non-translated leader sequence (Na2/tpi promoter) and the *Aspergillus niger* amyloglycosidase terminator (AMG terminator), the selective marker pyrG from *Aspergillus oryzae* enabling growth of a pyrG defective host, and the URA3 marker from *Saccharomyces cerevisiae* enabling growth of the pyrF defective *Escherichia coli* strain DB6507.

The *Aspergillus* expression vector pHUda737 was constructed in a following way:

The *A. oryzae* pyrG which encodes orotidine-5'-phosphate decarboxylase, an enzyme involved in the biosynthesis of uridine, was amplified using the primers opyrGF and opyrGR which introduce an XbaI and a SphI site respectively. They were designed based on the nucleotide sequences information of the *A. niger* genome database.

```
opyrGF:
tttctagacccaagccgctgctggaa       (SEQ ID NO: 18)

opyrGR
tttgcatgccgagcgtaaccgctgcctca    (SEQ ID NO: 19)
```

A PCR reaction with the genome DNA of the *Aspergillus oryzae* IFO4177 as template was performed with an Expand™ PCR system (Roche Diagnostics, Japan) using opyrGF and opyrGR. The amplification reactions (50 µl) were composed of 1 ng of template DNA per µl, 250 mM dNTP each, 250 nM primer pyrGF, 250 nM primer opyrGR, 0.1 U of Taq polymerase per µl in 1× buffer (Roche Diagnostics, Japan). The reactions were incubated in a DNA Engine PTC-200 (MJ-Research, Japan) programmed as follows: 1 cycle at 94° C. for 2 minutes; 30 cycles each at 92° C. for 1 minute, 55° C. for 1 minute, and 72° C. for 2 minutes; 1 cycle at 72° C. for 10 minutes; and a hold at 4° C.

The reaction products were isolated on a 1.0% agarose gel using TAE buffer where a 2.5 kb product band was excised from the gel and purified using a QIAquick™ Gel Extraction Kit (QIAGEN Inc., Valencia, Calif.) according to the manufacturer's instructions.

The 2.5 kb amplified DNA fragment was digested with XbaI and SphI, and ligated into the *Aspergillus* expression cassette pJaL790 digested with XbaI and SphI. The ligation mixture was transformed into *E. coli* DB6507 (ATCC 35673) using the *Saccharomyces cerevisiae* URA 3 gene as selective marker to create the expression plasmid pHUda737. The amplified plasmid was recovered using a QIAprep® Spin Miniprep kit (QIAGEN, Chatsworth, Calif.) according to the manufacturer's instructions.

The resultant plasmid was sequenced and compared to the public sequences database, showing that clones encode the *A. oryzae* pyrG gene.

Example 10

Construction of pHUda753 Expression Vector

Expression vector pHUda753 was constructed for transcription of the protease inhibitor gene from *Aspergillus oryzae*. The plasmid pJaL1000 harboring the protease inhibitor was digested with BamHI and XhoI. The 481 by fragment was gel-purified and ligated into the *Aspergillus* expression cassette pHUda737 digested with BamH I and XhoI. The ligation mixture was transformed into *E. coli* DB6507 (ATCC 35673) using the *Saccharomyces cerevisiae* URA 3 gene as selective marker to create the expression plasmid pHUda753.

The amplified plasmid was recovered using a QIAprep® Spin Miniprep kit (QIAGEN, Chatsworth, CA.) according to the manufacturer's instructions.

Plasmid pHUda753 comprised an expression cassette based on the *Aspergillus niger* neutral amylase II promoter fused to the *Aspergillus nidulans* triose phosphate isomerase non translated leader sequence (Na2/tpi promoter) and the *Aspergillus niger* amyloglycosidase terminator (AMG terminator), the selective marker pyrG from *Aspergillus oryzae* enabling growth of the pyrG defective mutant, and the URA3 marker from *Saccharomyces cerevisiae* enabling growth of the pyrF defective *Escherichia coli* strain DB6507.

Example 11

Description of the *Aspergillus* Plasmid pHUda667 for Expression of the V039 Protein For expression and secretion of the protein V039 the *Aspergillus niger* alpha-amylase signal where fused to V039. The gene was then cloned into the *Aspergillus* expression cassette pJaL790 resulting in plasmid pHUda667 (SEQ id NO: 20). The different elements in the sequence is described in table 2 below.

Plasmid pHUda667 is an expression cassette based on the *Aspergillus niger* neutral amylase II promoter fused to the *Aspergillus nidulans* triose phosphate isomerase non translated leader sequence (Na2/tpi promoter) and the *Aspergillus niger* amyloglycosidase terminator (AMG terminator), the selective marker amdS from *Aspergillus nidulans* enabling growth on acetamid as a sole nitrogen source and the URA3 marker from *Saccharomyces cerevisiae* enabling growth of the pyrF defective *Escherichia coli* strain DB6507.

TABLE 2

| Position (bp) | Size (bp) | Element | Origin |
|---|---|---|---|
| 1-1668 | 1597 | Pna2 | A. niger BO1 |
| 1669-1668 | 71 | Tpi | A. nidulans |
| 1669-1679 | 11 | Linker | Synthetic |
| 1680-1742 | 63 | SP288 signal | A. niger 31-26 |
| 1743-3056 | 1314 | AA | R. pusillus |
| 3057-3494 | 438 | CBM | A. niger BO1 |
| 3495-3515 | 21 | Linker | Synthetic |
| 3516-4207 | 692 | Tamg | A. niger BO1 |
| 4208-4213 | 6 | Linker | Synthetic |
| 4214-6929 | 2716 | amdS | A. nidulans |
| 6230-8096 | 1167 | pUC19 | E. coli. |
| 8097-8319 | 223 | Pura3 | S. cerevisiae. |
| 8320-9123 | 804 | URA3 | S. cerevisiae. |
| 9124-9204 | 81 | Tura3 | S. cerevisiae. |

Pna2 is modified neutral amylase II promoter from *Aspergillus niger*. The tpi is the 5' untranslated region of the *Aspergillus nidulans* triose phosphate isomerase (TPI) promoter.

AA is the *Rhizomucor pusillus* alpha-amylase.

Tamg is the amyloglycosidase terminator of *Aspergillus niger*.

pUC19 is a fragment of the pUC19 vector including the origin of replication. The origin of replication initiation site (colE1 origin) is in position 7357.

amdS is the acetamide gene (including promoter and terminator) from *A. nidulans*.

Pura3, URA3 and Tura 3 are the *S. cerevisiae* URA3 promoter, coding sequence and terminator respectively.

Example 12

Construction of an *Asperqillus niqer* Strain Expressing the Alpha-Amylase *A. niqer* CBM Fusion Protein in PM-8

*Aspergillus niger* strain PM-8 was transformed with plasmid pHUda667 as described under methods with the following modification that the Sodium nitrate was replaced with 10 mM acetamid for selection of transformants that can used acetamid as a nitrogen source and 20 mM uridine was added to the selection plates for complementing the pyrG minus geno-type of PM-8. One transformant which produce the Alpha-amylase CBM fusion protein was selected and named JaL1182.

Example 13

Expression of the Protease Inhibitor Genes Derived from *Asperqillus oryzae* and Alpha-Amylase CBM Fusion Protein *Asperqillus niqer* PM-8

*Aspergillus niger* strain PM-8 was transformed with plasmid pHUda667 and pHUda753 as described under methods with the following modification that the Sodium nitrate was replaced with 10 mM acetamid for selection of transformants that can used acetamid as a nitrogen source. Two transformant which's produce both the Alpha-amylase CBM fusion protein and the *A. oryzae* inhibitor was selected and named JaL1157 and 1158.

Example 14

Stability of the Alpha-Amylase CBM Fusion Protein in *Aspergillus* Strains JaL1157, JaL1158 and JaL1182

The strains JaL1157, JaL1158 and JaL1182 were inoculated into 100 ml of MLC medium and cultivated at 30° C. for 2 days. Ten ml of MLC medium was inoculated into 100 ml of MU-1 medium and cultivated at 30° C. for 7 days. Supernatants were obtained by centrifugation at 3,000×g for 10 minutes.

The pH of the supernatant was raised by adding a few drops of 0.05M NaOH up to pH 6.5-7.0 and incubated at 40° C. for 7 days. The incubated samples were subjected to a SDS-PAGE analysis.

SDS polyacrylamide electrophoresis was carried out using commercialized e-PAGEL gels ET 7.5L (ATTO Corporation). Ten μl of the incubated samples were suspended in 2× concentration of Sample Buffer (1% SDS, 1% beta-mercaptoethanol, 1 mg/ml Bromophenolblue, 10% Glycerol, 50 mM Tris-HCl {pH 6.8}) and boiled for 5 minutes. All the samples were loaded onto a polyacrylamide gel and subjected to electrophoresis in 1×Tris/Glycine/SDS running buffer (25 mM Tris-HCl, 0.1% SDS, 192 mM Glycine) at 20 mA for 90 min. Resulting gel was stained with Stain solution (1 g/L Coomassie brilliant blue, 10% acetic acid, 30% Methanol) for 30 min and then destained with destained solution (10% acetic acid, 30% Methanol) until the bands were visualized clearly.

Inspection of the gel showed that in strain JaL1182, in which no extra pepC inhibitor was produced, degradation products corresponding to alpha-amylase and CBM respectively were clearly visible, whereas in strains JaL1157 and JaL1158 very little degradation was observed.

The invention claimed is:

1. A method for producing a heterologous polypeptide of interest in an *Aspergillus* host cell comprising: (a) cultivating the *Aspergillus* host cell comprising a first recombinant nucleic acid sequence and a second recombinant nucleic acid sequence under conditions conducive for the expression of polypeptides encoded by the first recombinant nucleic acid sequence and second recombinant nucleic acid sequence, and wherein the first recombinant nucleic acid sequence encodes a heterologous polypeptide of interest and the second recombinant nucleic acid encodes an inhibitor polypeptide comprising an amino acid sequence having at least 90% sequence identity to the mature polypeptide of SEQ ID NO: 6, and wherein the inhibitor polypeptide is expressed by the *Aspergillus* host cell with an increased level of the inhibitor polypeptide compared to an *Aspergillus* host cell not comprising the first recombinant nucleic acid sequence and the second recombinant nucleic acid sequence.

2. The method of claim 1, wherein the inhibitor polypeptide comprises an amino acid sequence having at least 95% sequence identity to the mature polypeptide of SEQ ID NO: 6.

3. The method of claim 1, wherein the inhibitor polypeptide comprises an amino acid sequence having at least 99% sequence identity to the mature polypeptide of SEQ ID NO: 6.

4. The method of claim 1, comprising recovering the heterologous polypeptide.

5. The method of claim 1 wherein the heterologous polypeptide is an enzyme.

6. The method of claim 1 wherein the heterologous polypeptide is an antibody.

* * * * *